(12) United States Patent
Ren et al.

(10) Patent No.: US 11,524,977 B2
(45) Date of Patent: Dec. 13, 2022

(54) ULTRASOUND-ASSISTED SIMULATED DIGESTION METHOD OF MILK PROTEIN ACTIVE PEPTIDE AND APPLICATION THEREOF IN HEALTH FOODS

(71) Applicant: JIANGSU UNIVERSITY, Zhenjiang (CN)

(72) Inventors: Xiaofeng Ren, Zhenjiang (CN); Qiufang Liang, Zhenjiang (CN); Haile Ma, Zhenjiang (CN); Yuqing Duan, Zhenjiang (CN); Ronghai He, Zhenjiang (CN); Xiaoming Yang, Zhenjiang (CN); Xi Zhang, Zhenjiang (CN); Ting Hou, Zhenjiang (CN); Xinxiang Chen, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 201 days.

(21) Appl. No.: 16/632,546

(22) PCT Filed: Nov. 12, 2018

(86) PCT No.: PCT/CN2018/114969
§ 371 (c)(1),
(2) Date: Jan. 21, 2020

(87) PCT Pub. No.: WO2019/091472
PCT Pub. Date: May 16, 2019

(65) Prior Publication Data
US 2020/0157142 A1    May 21, 2020

(30) Foreign Application Priority Data

Nov. 13, 2017   (CN) .......................... 201711111423.0
Nov. 13, 2017   (CN) .......................... 201711111464.X (51) Int. Cl.
| | | |
|---|---|---|
| *C07K 1/36* | (2006.01) | |
| *A23L 33/18* | (2016.01) | |
| *C07K 5/103* | (2006.01) | |
| *C07K 14/47* | (2006.01) | |
| *C12P 21/06* | (2006.01) | |

(52) U.S. Cl.
CPC .............. *C07K 1/36* (2013.01); *A23L 33/18* (2016.08); *C07K 5/101* (2013.01); *C07K 14/4717* (2013.01); *C07K 14/4732* (2013.01); *C12P 21/06* (2013.01); *A23V 2002/00* (2013.01)

(58) Field of Classification Search
CPC ...... C07K 1/36; C07K 5/101; C07K 14/4717; C07K 14/4732; C12P 21/06
See application file for complete search history.

(56) References Cited

U.S. PATENT DOCUMENTS 5,952,193 A *   9/1999   Shimamura ............ A61K 38/01
                                                        435/68.1
9,877,995 B2 *  1/2018   Krauskopf ................ A61P 3/06

FOREIGN PATENT DOCUMENTS

| CN | 103130869 A | 6/2013 |
|---|---|---|
| CN | 105440103 A | 3/2016 |
| CN | 105524966 A | 4/2016 |
| CN | 107964034 A | 4/2018 |
| CN | 107964040 A | 4/2018 |
| WO | 2010125192 A1 | 11/2010 |

OTHER PUBLICATIONS

Yano et el., Biosci Biotech Biochem 60 (4) 661-663 1996 (Year: 1996).*
Yano. S. et. al. "Isolation from a-Zein of Thermolysin Peptides with Angiotensin I-Converting Enzyme Inhibitory Activity.", pp. 661-663, vol. 60. No. (4), Dec. 31, 1996 (Dec. 31, 1996), Biosci. Biotech. Biochem.
Stimson. E.R et. al. "Conformational Properties of Trans Ac-Asn-Pro-Tyr-NHMe and Trans Ac-Tyr-Pro-Asn-NHMe in Dimethylsulfoxide and in Water Determined by Multinuclear n.m.r. Spectroscopy.", pp. 569-582, vol. vol. 27, Dec. 31, 1986 (Dec. 31, 1986), Int. J. Peptide Protein Res.
Zhu, Qian et. al., "Progress in Research on Intestinal Absorption Mechanism of Milk-Derived ACE Inhibitory Peptides Using Caco-2 Cell Model", pp. 330-335, vol. 34, No. (9), Dec. 31, 2013 (Dec. 31, 2013), Food Science, China Academic Journal Electronic Publishing House.

(Continued)

*Primary Examiner* — Fred H Reynolds
*Assistant Examiner* — Joseph Fischer
(74) *Attorney, Agent, or Firm* — Soroker Agmon Nordman Pte Ltd (57) ABSTRACT

An ultrasound-assisted simulated digestion method of a milk protein active peptide and an application thereof in health foods, pertaining to the technical field of intensive processing of dairy products and preparation of health foods. The method firstly employs ultrasonic pretreatment of casein and β-lactoglobulin, followed by enzymatic hydrolysis with a protease to prepare casein and ρ-lactoglobulin polypeptide, and traces the activity of the polypeptide by simulating gastrointestinal digestion, and then simulates absorption by intestinal epithelial cells with Caco-2 cells, to characterize a highly active milk protein polypeptide digested by the gastrointestinal tract and absorbed by the Caco-2 cells simulating absorption by the inner wall of the small intestine. The method has identified five such highly active milk protein polypeptides.

5 Claims, 3 Drawing Sheets
Specification includes a Sequence Listing.

(56) References Cited

OTHER PUBLICATIONS

Li, Haiqin et. al., "Preliminary Study on Antibacterial Peptides in Casein Hydrolysates", pp. 147-148, vol. 32 No. 3 (Total 219), 2006, Food and Fermentat Ion Industries, China Academic Journal Electronic Publishing House.

M. Miguel, et. al., "ACE-inhibitory and antihypertensive properties of a bovine casein hydrolysate", Food Chemistry, 112 (2009) 211-214, Elsevier Ltd.

Q. Zhai, et. al., "Resear ch Advances of Antibacterial Peptides Derived from Bovine Casein", pp. 527-529, vol. 18, No. 3, May 2007, Letters in Biotechnology, China Academic Journal Electronic Publishing House.

A. Pellegrini, et. al., "Isolation and characterization of four bactericidal domains in the bovine L-lactoglobulin", Biochimica et Biophysica Acta 1526 (2001) 131-140, Elsevier Science B.V.

M. Murakami, et. al., "Structural Analysis of a New Anti-Hypertensive Peptide ($\beta$-Lactosin B) Isolated from a Commercial Whey Product", J. Dairy Sci., vol. 87, No. 7 (2004),1967-1974, American Dairy Science Association.

\* cited by examiner

SEQUENCE LISTING

<160> NUMBER OF SEQ ID NOS: 5

<210> SEQ ID NO 1
<211> LENGTH: 4
<212> TYPE: PRT
<213> ORGANISM: Cow
<220> FEATURE:
<223> OTHER INFORMATION: LQPP peptide

<400> SEQUENCE: 1

Leu Gln Pro Pro
1

<210> SEQ ID NO 2
<211> LENGTH: 3
<212> TYPE: PRT
<213> ORGANISM: Cow
<220> FEATURE:
<223> OTHER INFORMATION: APY peptide

<400> SEQUENCE: 2

```
Ala Pro Tyr
1

<210> SEQ ID NO 3
<211> LENGTH: 4
<212> TYPE: PRT
<213> ORGANISM: Cow
<220> FEATURE:
<223> OTHER INFORMATION: LSLP peptide

<400> SEQUENCE: 3

Leu Ser Leu Pro
1

<210> SEQ ID NO 4
<211> LENGTH: 4
<212> TYPE: PRT
<213> ORGANISM: Cow
<220> FEATURE:
<223> OTHER INFORMATION: FYQA peptide

<400> SEQUENCE: 4

Phe  Tyr  Gln  Ala
1

<210> SEQ ID NO 5
<211> LENGTH: 3
<212> TYPE: PRT
<213> ORGANISM: Cow
<220> FEATURE:
<223> OTHER INFORMATION: LQY peptide

<400> SEQUENCE: 5

Leu Gln Tyr
1
```

ULTRASOUND-ASSISTED SIMULATED DIGESTION METHOD OF MILK PROTEIN ACTIVE PEPTIDE AND APPLICATION THEREOF IN HEALTH FOODS

TECHNICAL FIELD

The present invention provides an innovative method for preparing bioactive peptides from milk protein using ultrasound-assisted enzymolysis coupled to simulated gastrointestinal (GI) digestion and absorption. The invention belongs to the technical field of deep processing of dairy products and preparation of functional food, and the prepared bioactive peptides can be useful in the preparation of functional foods or nutraceuticals.

BACKGROUND ART

Hypertension refers to a persistently elevated systemic arterial blood pressure, i.e. a systolic blood pressure ≥140 mm Hg and a diastolic blood pressure ≥90 mm Hg. Typically, hypertension is associated with clinical or functional impairment of the heart, brain, kidney and other organs.

Hypertension is the most common chronic disease in the world and is the most important risk factor for cardiovascular and cerebrovascular diseases. Angiotensin converting enzyme (ACE EC 3.4.15.1) is a dipeptide exopeptidase containing $Zn^{2+}$ with a molecular weight between $1.29 \times 10^5$-$1.36 \times 10^5$ Da, and is widely distributed in human tissues and blood. ACE is a key enzyme in the renin angiotensin system (RAS), responsible for conversion of angiotensin (Ang) I into Ang II, a vasoconstrictor leading to elevated blood pressure. Inhibition of ACE activity is considered to be an important and effective method for the treatment of hypertension. Pharmaceutical drugs targeting ACE have proven successful in lowering high blood pressure; however, food-derived ACE inhibitors are believed to be safer than pharmaceutical drugs due to the avoidance of some drug-associated adverse side effects, such as cough, angioedema, et al. Therefore, development of natural ACE inhibitors for the treatment and prevention of hypertension and cardiovascular diseases has become a very popular research topic.

Chronic inflammation is an underlying contributor to various chronic diseases. Endothelial cells, lining the inner layer of blood vessels, play a vital role in vascular biology, such as regulation of blood vessel tone, hemostasis, neutrophil recruitment, hormone trafficking, and fluid filtration. Vascular inflammation is a key factor that contributes to endothelial dysfunction and has been linked to a variety of disease states, including atherosclerosis, diabetes mellitus, coronary artery disease, hypertension, and hypercholesterolemia. At present, the clinical treatment medicine for inflammation mainly include steroids and non-steroids. Yet there are concerns about the side effects of long-term use of these drugs. The consumption of these drugs also requires a large economic investment. As a result, there has been a substantial increase in public and scientific awareness about natural compounds and their derivatives as safer alternatives to anti-inflammatory drugs.

Casein, a milk protein is usually prepared by precipitating skim milk at the pH and temperature of 4.6 and 20° C., respectively. The total amount of the protein in milk is about 3.3%, of which about 2.5% is casein. Casein is one of a group of secreted calcium (phosphate) binding phosphoproteins; it mainly exists in five forms: $\alpha_{s1}^-$, $\alpha_{s2}^-$, $\beta^-$, $\kappa^-$ and $\gamma^-$ casein, which account for 38%, 10%, 36%, 13% and 3% of the total casein, respectively. Many studies showed that a large amount of casein in milk exists in the form of casein micelles, which are aggregated by calcium caseinate-calcium phosphate system with a diameter of 10-300 nm. Casein is widely used as a nutrient enhancer, thickener, and emulsifier in different food products. However, casein is not easily digested and absorbed in the human body, and its solubility is very low under low acid and acidic conditions, which also limits its application in the food industry.

Casein is also claimed as a good source of bioactive peptides. Many studies have reported that enzymatic hydrolysis of casein could produce a large number of peptides with biological activity. Miguel et al. reported that a pepsin hydrolysed bovine casein (HBC) showed potent ACE-inhibitory activity, and was 10 times higher in the HBC fraction with molecular mass lower than 3000 Da (Miguel M, Contreras M M, Recio I, et al. ACE-inhibitory and antihypertensive properties of a bovine casein hydrolysate [J]. Food Chemistry, 2009, 112(1):211-214). Zhai Qingxin et al. purified and isolated some bioactive peptides from the enzymatic hydrolysate of casein, and these peptides exhibited excellent antimicrobial activity against *Staphylococcus aureus* and *Escherichia coli* (Zhai Qingxin, Zhang Yuanshu. Research Advances of Antibacterial Peptides Derived from Bovine Casein [J]. Biotechnology Communication, 2007, 03: 527-529). Li Haiqin et al. hydrolyzed casein as a raw material with trypsin under appropriate conditions and ultrafiltered through an ultrafiltration membrane to isolate peptides with strong antibacterial activity. The results showed the great inhibitory activity of these peptides against a number of microorganisms, especially *Staphylococcus aureus* and *Escherichia coli*. Bioactive peptides released from casein have great potential as functional food/nutraceutical ingredients for improving human health.

There are many methods for preparing food-derived peptides with high biological activity, mainly focusing on the optimization of enzymatic hydrolysis processes, and the separation and purification of peptides. To exert physiological activity in vivo, bioactive peptides must be absorbed into the blood circulation and reach target organs in an active form after extensive gastrointestinal (GI) digestion. As we know, the GI tract contains a large amount of pepsin and trypsin. Bioactive peptides are expected to be taken orally; the bioactive peptides obtained by the above methods are also composed of amino acids and are susceptible to proteases present in the GI tract. At the same time, the epithelium of the small intestine cells has multiple pathways for the absorption of peptides, such as transport through the gut epithelium, passive diffusion across cells, and cell bypass transport. It is very important to investigate the digestion and absorption in the GI tract of the body for the preparation of bioactive peptides. As described in the Chinese patent "The anti-inflammatory peptides isolated from the viscera of abalone in a wrinkled dish and its use" (201510594885.7), the anti-inflammatory peptides were prepared by the method of simulated GI digestion, but its absorption by intestinal epithelium was ignored. Therefore, the absorption of peptides by intestinal epithelium was ignored in current methods for preparing functional peptides from casein. It cannot truly be simulated to prepare the bioactive peptides by enzymolysis combined with GI digestion and absorption.

β-Lactoglobulin (β-LG) (~68%) is the main fraction of whey proteins, which account for about 10% of total proteins in bovine milk. β-LG with 18277~18363 Da is predominantly in the form of a dimer consisting of two monomeric subunits joined by non-covalent bonds; each monomer contains two disulfide bonds, from residues Cys-106 to Cys-119 and from Cys-66 to Cys-160, as well as a free sulfhydryl Cys121. Recent studies have found that β-LG is a good source of bioactive peptides; β-LG-derived peptides were reported to possess excellent antihypertensive activity, ACE inhibitory activity, antibacterial activity, lower serum cholesterol levels, and sedative, analgesic, and soothing effects. Murakami et al. found a tetrapeptide (ALPM) derived from β-LG with strong ACE inhibitory activity. Four peptides obtained by enzymolysis of β-LG exhibited strong antibacterial activity; they were VAGTWY f(15-20), AASDISLLDAQSAPLR f(2540), IPAVFK f(78-83), VLVLDTDYK f(92-100). However, there have been few reports on the anti-inflammatory activity of β-LG-derived peptides on the vascular endothelium, and there have been no reports on the preparation of β-LG-derived peptides having anti-inflammatory activity.

There are many methods for preparing β-LG-derived peptides with high biological activity, by mainly focusing on the optimization of enzymatic hydrolysis processes, the separation, and purification of the peptides. To exert physiological activity in vivo, bioactive peptides must be absorbed into the blood circulation to reach the target organs in an active form after extensive gastrointestinal (GI) digestion. As we know, the GI tract contains a large amount of pepsin and trypsin. Bioactive peptides are expected to be taken orally; the bioactive peptides obtained by the above methods are also composed of amino acids and are susceptible to proteases present in the GI tract. At the same time, the epithelium of the small intestine cells has multiple pathways for the absorption of peptides, such as transport through the gut epithelium, passive diffusion across cells, and cell bypass transport. It is very important to research on digestion and absorption in the GI tract of the body for the preparation of bioactive peptides. As described in the Chinese patent, "The anti-inflammatory peptides isolated from the viscera of abalone in a wrinkled dish and its use" (201510594885.7), the anti-inflammatory peptides were prepared by the method of simulated GI digestion, but its absorption by intestinal epithelium was not studied. Therefore, the absorption of peptides by intestinal epithelium was ignored in current methods for preparing functional peptides from β-LG. It cannot truly be simulated to prepare the bioactive peptides by enzymolysis combined with GI digestion and absorption.

SUMMARY

In view of the above deficiencies, the present invention first used ultrasound pretreatment of casein, followed by enzymatic hydrolysis to prepare peptides with ACE inhibitory activity, and then studied the stability of the ACE inhibitory activity of the casein-derived peptides in simulated GI digestion, and finally screened and characterized the peptides with high ACE-inhibitory activity after absorption by Caco-2 cells simulating the small intestine.

The objective of the present invention was to identify three new ACE-inhibitory peptides from casein hydrolysate after simulated GI digestion and transport in Caco-2 cells firstly.

The amino acid sequence of the three new ACE-inhibitory peptides:
Leu-Gin-Pro-Pro (SEQ ID No. 1);
Ala-Pro-Tyr (SEQ ID No. 2):
Leu-Ser-Leu-Pro (SEQ ID No. 3).

The present invention also sought to provide an innovative method for preparing casein-derived bioactive peptides using ultrasound-assisted enzymolysis coupled to simulated GI digestion and absorption. The steps of the method are as follows:

(1) Ultrasound treatment of casein. Casein with a concentration of 1 g/100 mL-5 g/100 mL was prepared by dissolving in a phosphate buffer (pH 7.8). The above concentration of casein suspension was treated by ultrasound equipment.

(2) Enzymolysis of casein. After ultrasound treatment, the casein suspensions were preheated to 50° C.-70° C. and adjusted to pH 7.5-8.0 with 1.0 M NaOH. Alcalase (the ratio of E/S was 1:20-1:50) (w/w) was added to initial the reaction and the enzymolysis time was 2-4 h. The mixture was heated and maintained at 100° C. for 10 min to terminate the reaction. Then the mixture was adjusted to pH 7.0 and centrifuged, the supernatant was collected, desalted, concentrated, and freeze-dried to a powder.

(3) Simulated GI digestion. Casein-derived hydrolysate were subjected to simulated gastric and intestinal digestion. Simulated gastric and intestinal fluids were prepared according to the U.S. Pharmacopeia. Briefly, casein-derived hydrolysate were digested with gastric fluid at 1:20-1:50 (w/v) for 2-4 h in a shaking incubator with 120-180 rpm at 37° C. Then the pH was adjusted to 6.8 and pancreatin was added at 1:100 (w/v) to form the intestinal fluid. The mixture was incubated for 4-6 h to mimic intestinal digestion. The digestion was terminated in boiling water for 10 min. The digests were allowed to cool down and centrifuged at 10,000 g for 10 min to collect the supernatant, which was further centrifuged, desalted, concentrated, and freeze-dried to a powder.

(4) Simulated intestinal epithelium absorption. The Caco-2 cells transport model was well constructed. A concentration of 20 mg/mL casein hydrolysate digest was prepared by dissolving in an HBSS buffer. Absorption of the casein hydrolysate digests was evaluated by adding the digests to the apical (AP) surface. Basal (BL) surface samples at 0.5-4 h were collected, desalted, concentrated, and freeze-dried.

(5) Characterization of the casein-derived peptides. The casein-derived peptides absorbed by Caco-2 cells in step (4) were subjected to liquid chromatography-electrospray ionization tandem mass spectrometry (LC-ESI-MS/MS) analysis. Peptides with less than 500 Da were selected.

(6) The selected peptides in step (5) were synthesized and assayed for their ACE-inhibitory activity. Three casein-derived peptides showed excellent ACE-inhibitory activity and the corresponding amino acid sequences were:
Leu-Gln-Pro-Pro (SEQ ID No. 1);
Ala-Pro-Tyr (SEQ ID No. 2);
Leu-Ser-Leu-Pro (SEQ ID No. 3).

The ultrasound treatment conditions in the step (1) are as follows: treatment time, 10 min-30 min; intermittent ratio 10 s/3 s; temperature 25° C.-40° C. Single-frequency ultrasound at 20, 40 and 60 kHz, dual-frequency simultaneous ultrasound at 20/40, 20/60 and 40/60 kHz and triple-frequency simultaneous ultrasound at 20/40/60 kHz were used for the sample treatment.

The protease used in the step (2) may be either alcalase, papain, neutral protease, alcalase, and thermolysin; thermolysin is preferred.

Among the three casein-derived peptides described in the step (5), the peptide having the amino acid sequences Leu-Gln-Pro-Pro (SEQ ID No. 1) is preferable.

The above three casein-derived ACE-inhibitory peptides could be very useful in functional foods. A capsule or tablet containing the peptides produced by a known method can be used as functional foods or nutraceuticals for assisting blood pressure lowering.

Another aspect of the present invention is to characterize anti-inflammatory peptides from β-LG. The β-LG was firstly treated with ultrasound, followed by hydrolysis to prepare peptides with anti-inflammatory activity. Then the stability of the anti-inflammatory activity of the β-LG-derived peptides in simulated GI digestion was studied. Finally the peptides with high anti-inflammatory properties after absorption by Caco-2 cells in the simulated small intestine were screened and characterized.

The present invention also sought to identify two new anti-inflammatory peptides from β-LG hydrolysate after simulated GI digestion and transport in Caco-2 cells.

The amino acid sequence of the two new anti-inflammatory peptides:
Phe-Tyr-Gln-Ala (SEQ ID No. 4);
Leu-Gln-Tyr (SEQ ID No. 5).

The present invention also aimed to provide an innovative method for preparing β-LG-derived bioactive peptides using ultrasound-assisted enzymolysis coupled to simulated GI digestion and absorption. The steps of the method are as follows:

(1) Extraction of β-LG. A concentration of 7% (w/v) whey protein solution was prepared by adding whey protein to 7% NaCl water, adjusting the pH to 2 with HCL, and centrifuging at 5000 rpm for 20 min to collect the supernatant. Then the supernatant was dialyzed using a dialysis bag with a molecular weight cut off of 14000 Da, placed in 30 volumes of distilled water for 20 h, and the retentate in the dialysis bag, i.e. β-LG, was collected.

(2) Ultrasound treatment of β-LG. The casein with a concentration of 1 g/mL-4 g/mL was prepared by dissolving in a phosphate buffer (pH 7.8). The above concentration of casein suspension was treated by ultrasound equipment.

(3) Enzymolysis of s-LG. After ultrasound treatment, the β-LG suspensions were preheated to 50° C.-70° C. and adjusted to pH 7.5-8.0 with 1.0 M NaOH. Alcalase (the ratio of E/S was 1:20-1:50) (w/w) was added to initial the reaction and the enzymolysis time was 2-4 h. The mixture was heated and maintained at 100° C. for 10 min to terminate the reaction. Then the mixture was adjusted to pH 7.0 and centrifuged; the supernatant was collected, desalted, concentrated, and freeze-dried to a powder.

(4) Simulated GI digestion. β-LG-derived hydrolysate was subjected to simulated gastric and intestinal digestion. Simulated gastric and intestinal fluids were prepared according to the U.S. Pharmacopeia. Briefly, β-LG-derived hydrolysate was digested with gastric fluid at 1:20-1:50 (w/v) for 2-4 h in a shaking incubator with 120-180 rpm at 37° C. Then the pH was adjusted to 6.8 and pancreatin was added at 1:100 (w/v) to form the intestinal fluid. The mixture was incubated for 4-6 h to mimic intestinal digestion. The digestion was terminated in boiling water for 10 min. The digest was cooled down and centrifuged at 10,000 g for 10 min to collect the supernatant, which was further centrifuged, desalted, concentrated, and freeze-dried to a powder.

(5) Simulated intestinal epithelium absorption. The Caco-2 cells transport model was well constructed. A concentration of 20 mg/mL β-LG hydrolysate digest was prepared by dissolving in an HBSS buffer. Absorption of the casein hydrolysate digests was evaluated by adding the digests to the apical (AP) surface. Basal (BL) surface samples at 0.5-4 h were collected, desalted, concentrated, and freeze-dried.

(6) Characterization of the β-LG derived peptides. The β-LG derived peptides absorbed by Caco-2 cells in step (5) were subjected to liquid chromatography-electrospray ionization tandem mass spectrometry (LC-ESI-MS/MS) analysis. The peptides with less than 500 Da were selected out.

(7) The selected peptides in step (6) were synthesized and assayed for their anti-inflammatory activity. Two β-LG-derived peptides showed excellent inflammatory activity and the corresponding amino acid sequences were:
Phe-Tyr-Gln-Ala (SEQ ID No. 4);
Leu-Gln-Tyr (SEQ ID No. 5).

The ultrasound treatment conditions in the step (2) are as follows: treatment time, 10 min-30 min; intermittent ratio 10 s/3 s; temperature 25° C. Single-frequency ultrasound with 20, 28 and 40 kHz, dual-frequency simultaneous ultrasound with 20/40, 20/28 and 28/40 kHz and triple-frequency simultaneous ultrasound with 20/28/40 kHz were used for the sample treatment.

The protease used in the step (3) may be alcalase, neutral protease, or thermolysin; the thermolysin is preferred.

For the two casein-derived peptides described in the step (6), the peptide having the amino acid sequences Leu-Gln-Tyr (SEQ ID No. 5) is preferable.

The two β-LG-derived anti-inflammatory peptides could be well suited for functional foods. A capsule or tablet containing the above peptides produced by a known method can be used in functional foods or nutraceuticals for assisting blood pressure lowering.

The advantages of the invention are:

(1) The present invention discloses for the first time an innovative method for characterizing and isolating casein-derived peptides having high ACE-inhibitory activity. The peptides obtained by this method can survive GI digestion and can be directly absorbed by intestinal epithelial cells.

(2) The present invention discloses for the first time an amino acid sequence of three casein-derived peptides having high ACE-inhibitory activity against GI digestion and that can be directly absorbed by intestinal epithelial cells.

(3) The present invention utilizes simulated GI digestion in combination with simulated intestinal epithelial cell absorption for the first time to study the ACE-inhibitory activity of casein-derived hydrolysate;

(4) The present invention for the first time studied the absorption of the casein-derived hydrolysate digest in the Caco-2 cells.

(5) The present invention discloses for the first time an amino acid sequence of two β-LG-derived peptides having excellent anti-inflammatory activity against GI digestion, and that can be directly absorbed by intestinal epithelial cells.

(6) The present invention discloses for the first time an innovative method for characterizing and isolating β-LG-derived peptides having high anti-inflammatory activity. Further, the peptides obtained by this method can survive GI digestion and be directly absorbed by intestinal epithelial cells.

(7) The present invention for the first time studied the absorption of the β-LG-derived hydrolysate digest in the Caco-2 cells.

(8) The present invention for the first time reported the β-LG-derived hydrolysate exhibited good anti-inflammatory activity on vascular endothelial cells.

EMBODIMENTS

1. Experimental Method

1.1. Degree of Hydrolysis (DH) and Protein Conversion Rate

The DH of casein was determined using the pH-state method, DH is defined as the percentage of cleaved peptide bonds, which was calculated using the equation below:

$$DH\ (\%) = \frac{V \times N}{\alpha \times M \times h_{tot}} \times 100\%$$

Where, V is the titrant volume of NaOH (mL), N is the concentration of NaOH (mol/L), a is the degree of dissociation of $\alpha\text{-}NH_2$ (0.985 for casein), M is the mass of protein (g), and $h_{tot}$ is the number of peptide bonds in the substrate; different proteins had different values of $h_{tot}$ the empirical value of casein is $h_{tot}$=7.35 mol/g.

The total nitrogen content of the casein protein and its derived hydrolysate was determined by the Kjeldahl method, and the conversion rate of casein was calculated as follows:

Protein conversion rate (%)=hydrolysate nitrogen content/substrate protein nitrogen content*100%.

1.2 Measurement of ACE Inhibitory Activity

The FAPGG was used as the substrate of ACE, each reaction component was added according to the Table, and the ACE inhibition rate of the sample was measured with a microtiter plate reader at 340 nm.

Where $X_1$ is the absorbance of the control group without protein hydrolysates before reaction, $Y_1$ is the absorbance of the sample group before the reaction, $X_2$ is the absorbance of the blank group after the reaction, and $Y_2$ is the absorbance of the sample group after the reaction. The test was performed five times. The ACE inhibitory activity was calculated as follows:

The ACE inhibitory rate (%)=100−($\Delta A_{sample}$)/($\Delta A_{blank}$)×100%

$\Delta A_{sample}$=$X_1$−$X_2$, $\Delta A_{blank}$=$Y_1$−$Y_2$.

| | Measurement of ACE inhibitory activity | |
|---|---|---|
| | Blank (μL) | Sample (μL) |
| ACE (0.1 U/mL) | 10 | 10 |
| FAPGG (1 mmol/L) * | 50 | 50 |
| Matrix buffer ** | 40 | 0 |
| ACE inhibitor | 0 | 40 |

Note:
FAPGG (1.0 mmol/L) was prepared by taking 3.994 mg of FAPGG plus matrix buffer, making up to 10 mL, dissolving and mixing, and then storing at 4° C. in the dark. Matrix buffer ** was prepared by dissolving 1.910 g of HEPES and 1.755 g of NaCl in double distilled water, adjusting the pH to 8.3 with NaOH, and replenishing the water to 100 mL, and storing at 4° C. for later use.

1.3 Cell Culture

The human colon adenocarcinoma cell line, Caco-2 (HTB-37™) was obtained from American-type culture collection (ATCC. Manassas. Va., USA). The cells were grown in Dulbecco's Modified Eagle's Medium (DMEM) supplemented with 10% fetal bovine serum, 2.5% HEPES, 1% non-essential amino acids and 1% antibiotics. Cells were incubated at 37° C. in a humidified atmosphere (5% $CO_2$). The medium was replaced three times a week, and the cells were subcultured (at 80-90% confluence) by using 0.25% trypsin-EDTA treatment before use in the experiments.

1.4 Measurement of Cytotoxicity

The cell cytotoxic properties were monitored using an Alamar Blue assay. Briefly, Caco-2 cells were grown in 96-well plates at a density of $1\times10^4$ cell/well for 24 h. After 24 h, the medium was changed and the cells were treated with various concentrations (10-50 mg/nil) of casein hydrolysate for another 24 h. After 24 h treatment, the media was discarded, and the fresh medium with 10% Alamar Blue reagent was added and incubated for an additional 4 h at 37° C. The fluorescence intensity of the wells was measured at an excitation wavelength of 560 nm and an emission wavelength of 590 nm. Cell viability is expressed as a percentage compared to untreated cells.

1.5 Simulated Intestinal Epithelium Absorption Using Caco-2 Cells

The samples collected from the AP and BL surfaces of Caco-2 cells were analyzed on an Acquity Ultra-Performance Liquid Chromatograph (UPLC) system with an Acquity UPLC BEH $C_{18}$ column (100 mm×2.1 mm i.d., 1.7 μm, Waters, Milford, Mass., USA) using an injection volume of 15 μL. Mobile phases were solvent A (1% TFA in Milli-Q water) and solvent B (1% TFA in acetonitrile). The peptides were eluted with a gradient of solvent A (100-75% in 25 min, 75-50% in 25-35 min) at a flow rate of 0.3 m/min. The elution was monitored at 220 nm. Absorption was expressed as the percentage of total peak area calculated at different time points (0.5 h, 1 h, 2 h and 4 h) in the BL surface as compared to 0 h in the AP surface.

1.6 Identification of Casein-Derived Peptides Using UPLC-MS

The liquid chromatography column used in this study was nanoACQUITY BEH130 $C_{18}$ (75 μm×50 mm, 1.7 μm. The solvent A was acetonitrile (ACN) containing 0.1% formic acid. The peptides were separated using the following gradient: increasing solvent B containing water with 0.1% formic acid from 1% to 6% B in 2 min, to 25% B in 23 min. to 45% B in 15 min. to 75% B in 5 min, to 95% B in 5 min, and keeping at 95% B for 5 min. The mass spectrometer was operated in a positive mode with a capillary voltage of 3.5 kV and a source temperature of 100° C. Spectra were recorded over the m/z ranges of 200-1000 in MS mode and in 50-1990 MS/MS mode. The amino acid sequences of peptides were analyzed using Mass Lynx software (Micromass U.K. Ltd.). Peaks Viewer 4.5 (Bioinformatics Solutions Inc., Waterloo, ON, Canada), in combination with manual de novo sequencing was used to process the MS/MS data. Identified peptide sequences were synthesized (>98% purity) by Genscript Corp (Piscataway, N.J.) and used for the bioactivity assays.

Example 1

Ultrasound treatment of casein. Casein with a concentration of 1 g/100 mL was prepared by dissolving in a phosphate buffer (pH 7.8). The above concentration of casein suspension was treated by ultrasound equipment. The ultrasound treatment conditions are as follows: treatment time 30 min, intermittent ratio 10 s/3 s; temperature 25° C. Single-frequency ultrasound with 40 kHz was used for the sample treatment.

Enzymolysis of casein. After ultrasound treatment, the casein suspensions were preheated to 50° C. and adjusted to pH 8.0 with 1.0 M NaOH. Alcalase (the ratio of E/S was 1:20)(w/w) was added to initialize the reaction, and the enzymolysis time was 2 h. The mixture was heated and maintained at 100° C. for 10 min to terminate the reaction. Then the mixture was adjusted to pH 7.0 and centrifuged; the supernatant was collected, desalted, concentrated, and freeze-dried to a powder. The DH and protein conversion rate (CR) of the casein, and the ACE inhibitory activity of the casein-derived hydrolysate were determined.

Simulated gastrointestinal digestion. Simulated gastric and intestinal fluids were prepared according to the U.S. Pharmacopeia (USP30-NF25). Briefly, Casein-derived hydrolysates were digested with gastric fluid at 1:20 (w/v) for 4 h in a shaking incubator with 120 rpm at 37° C. Then the pH was adjusted to 6.8 and pancreatin was added at 1:100 (w/v) to form the intestinal fluid. The mixture was incubated for a further 6 h to mimic intestinal digestion. The digestion was terminated in boiling water for 10 min. The digests were allowed to cool down and were centrifuged at 10,000 g for 10 min to collect the supernatant, which was further centrifuged, desalted, concentrated, and freeze-dried to a powder. The ACE inhibitory activity of the 4 h's and 10 h's casein hydrolysate digest was measured.

As shown in Table 1, after ultrasound pretreatment, the DH of casein increased from 10.02% to 16.54%, and the protein conversion rate increased from 30.10% to 44.08%. The ACE inhibitory activity of casein hydrolysate, as shown by $IC_{50}$ value, was decreased from 64.21 µg/mL to 52.13 µg/mL, indicating ultrasound pretreatment largely improved the ACE inhibitory activity of casein hydrolysate. After simulated gastric digestion and simulated intestinal digestion, the casein hydrolysate digest showed good ACE inhibitory activity, while the $IC_{50}$ values were 49.21 µg/mL and 55.19 µg/mL, respectively (Table. 2). The above results indicate that the casein-derived hydrolysate exhibits excellent ACE inhibitory activity after simulated GI digestion.

Example 2

Ultrasound treatment of casein. Casein with a concentration of 2 g/100 mL was prepared by dissolving in a phosphate buffer (pH 7.8). The above concentration of casein suspension was treated by ultrasound equipment. The ultrasound treatment conditions are as follows: treatment time 20 min; intermittent ratio 10 s/3 s; temperature 30° C. Dual-frequency simultaneous ultrasound treatments of 20/40 kHz were used for the sample treatment.

Enzymolysis of casein. After ultrasound treatment, the casein suspensions were preheated to 55° C. and adjusted to pH 8.0 with 1.0 M NaOH. Neutral protease (the ratio of E/S was 1:30) (w/w) was added to initialize the reaction, and the enzymolysis time was 4 h. The mixture was heated and maintained at 100° C. for 10 min to terminate the reaction. Then the mixture was adjusted to pH 7.0 and centrifuged; the supernatant was collected, desalted, concentrated, and freeze dried to a powder. The DH and CR of the casein, and the ACE inhibitory activity of the casein-derived hydrolysate was determined.

Simulated gastrointestinal digestion. Simulated gastric and intestinal fluids were prepared according to the U.S. Pharmacopeia (USP30-NF25). Briefly, Casein-derived hydrolysates were digested with gastric fluid at 1:30 (w/v) for 3 h in a shaking incubator with 150 rpm at 37° C. Then the pH was adjusted to 6.8 and pancreatin was added at 1:100 (w/v) to form the intestinal fluid. The mixture was incubated for a further 4 h to mimic intestinal digestion. The digestion was terminated in boiling water for 10 min. The digests were allowed to cool down and centrifuged at 10,000 g for 10 min to collect the supernatant, which was further centrifuged, desalted, concentrated, and freeze-dried to a powder. The ACE inhibitory activity of the 4 h's and 10 h's casein hydrolysate digest was measured.

As shown in Table 1, after dual-frequency simultaneous ultrasound pretreatment, the DH of casein increased from 5.21% to 9.45%, and the protein conversion rate increased from 18.11% to 22.39%. The ACE inhibitory activity of casein hydrolysate indicated by $IC_{50}$ value was decreased from 100.23 µg/mL to 95.21 µg/mL, indicating ultrasound pretreatment largely improved the ACE inhibitory activity of casein hydrolysate. After simulated gastric digestion, the casein hydrolysate digest showed good ACE inhibitory activity; its $IC_{50}$ value was 72.11 µg/mL; after simulated intestinal digestion, the casein hydrolysate digest still showed good ACE inhibitory activity, and its $IC_{50}$ value was 79.03 µg/mL (Table. 2). The above results indicate that the casein-derived hydrolysate still exhibited excellent ACE inhibitory activity after simulated GI digestion.

Example 3

Ultrasound treatment of casein. Casein with a concentration of 5 g/100 mL was prepared by dissolving in a phosphate buffer (pH 7.8). The above concentration of casein suspension was treated by ultrasound equipment. The ultrasound treatment conditions are as follows: treatment time 10 min; intermittent ratio 10 s/3 s; temperature 40° C. Triple-frequency simultaneous ultrasound treatments of 20/40/60 kHz were used for the sample treatment.

Enzmylosis of casein. After ultrasound treatment, the casein suspensions were preheated to 70° C. and adjusted to pH 8.0 with 1.0 M NaOH. Papain (the ratio of E/S was 1:50) (w/w) was added to initialize the reaction, and the enzymolysis time was 2 h. The mixture was heated and maintained at 100° C. for 10 min to terminate the reaction. Then the mixture was adjusted to pH 7.0 and centrifuged; the supernatant was collected, desalted, concentrated, and freeze-dried to a powder. The DH and CR of the casein, and the ACE inhibitory activity of the casein-derived hydrolysate were determined.

Simulated gastrointestinal digestion. Simulated gastric and intestinal fluids were prepared according to the U.S. Pharmacopeia (USP30-NF25). Briefly, Casein-derived hydrolysates were digested with gastric fluid at 1:50 (w/v) for 4 h in a shaking incubator with 180 rpm at 37° C. Then the pH was adjusted to 6.8 and pancreatin was added at 1:100 (w/v) to form the intestinal fluid. The mixture was incubated for a further 6 h to mimic intestinal digestion. The digestion was terminated in boiling water for 10 min. The digests were allowed to cool down and centrifuged at 10,000 g for 10 min to collect the supernatant, which was further centrifuged, desalted, concentrated, and freeze-dried to a powder. The ACE inhibitory activity of the 4 h's and 10 h's casein hydrolysate digest was measured.

As shown in Table 1, after triple-frequency ultrasound pretreatment, the DH of casein increased from 7.21% to 11.36%, the protein conversion rate increased from 21.98% to 26.02%. The $IC_{50}$ value of ACE inhibitory activity of casein hydrolysate was decreased from 97.32 µg/mL to 90.11 µg/mL, indicating ultrasound pretreatment largely improved the ACE inhibitory activity of casein hydrolysate.

After simulated gastric digestion, the casein hydrolysate digest showed good ACE inhibitory activity, its $IC_{50}$ value was 65.32 µg/mL; after simulated intestinal digestion, the casein hydrolysate digest still showed good ACE inhibitory activity, its $IC_{50}$ value was 60.31 µg/mL (Table. 2). The above results indicate that the casein derived hydrolysate still exhibited excellent ACE inhibitory activity after simulated GI digestion.

as follows: Caco-2 cells were grown in 12-well Transwell® plates at a concentration of $2\times10^5$ cells/mL. The medium of the cell was replaced every other day. After 21 days of cell culture, some evaluation indicators of the Caco-2 cells were measured, including epithelial cell resistance, alkaline phosphatase activity, and sodium fluorescein leakage test. Before initiation of the transport experiments, the Caco-2 cells were washed by an HBSS buffer; and 0.5 mL of the casein hydrolysate digest (20 mg/mL, dissolved in an HBSS buffer) was added to the AP surface; 1.5 mL of HBSS buffer was added to the BL surface; finally, the Caco-2 cells were incubated for 4 h at 37° C. 0.2 mL of AP surface samples at 0 h and BL surface samples at 0.5, 1, 2, and 4 h were collected for the absorption detection. The AP (apical) surface samples and BL (basolateral) surface samples at 4 h were collected for the ACE inhibitory activity detection, respectively. The casein hydrolysates digests and their absorbed digests were subjected to the amino acid sequences analysis by UPLC-MC. Some small peptides with strong ionic strength were screened out, synthesized, and detected for ACE inhibitory activity.

TABLE 1

Effects of ultrasound pretreatment on the DH, CR and ACE inhibitory activity of casein hydrolysates by different enzymatic hydrolysis

| | Traditional hydrolysis | | | Ultrasound assisted hydrolysis | | | |
| --- | --- | --- | --- | --- | --- | --- | --- |
| Enzyme | DH (%) | CR (%) | $IC_{50}$ of ACE inhibitory activity (µg/mL) | Ultrasound mode | DH (%) | CR (%) | $IC_{50}$ of ACE inhibitory activity (µg/mL) |
| Alcalase | 10.02 ± 1.78 | 30.10 ± 0.91 | 64.21 ± 9.12 | 40 kHz | 16.54 ± 0.99 | 44.08 ± 0.59 | 52.13 ± 6.11 |
| Neutral protease | 5.21 ± 0.52 | 18.11 ± 0.37 | 100.23 ± 14.98 | 20/40 kHz | 9.45 ± 0.27 | 22.39 ± 0.37 | 95.21 ± 8.0 |
| Papain | 7.21 ± 0.49 | 21.98 ± 0.64 | 97.32 ± 10.43 | 20/40/60 kHz | 11.36 ± 1.18 | 26.02 ± 0.64 | 90.11 ± 11.34 |

TABLE 2

Effects of different casein hydrolysates before gastric digestion, after gastric digestion, intestinal digestion and Caco-2 cells absorption on ACE inhibitory activity

| | $IC_{50}$ of ACE inhibitory activity (µg/mL) | | | |
| --- | --- | --- | --- | --- |
| Casein-derived hydrolysates | Before gastric digestion | After gastric digestion | After intestinal digestion | After Caco-2 cells absorption |
| Alcalase hydrolysates | 52.13 ± 6.11 | 49.21 ± 4.91 | 55.19 ± 5.72 | 21.37 ± 2.07 |
| Neutral protease hydrolysates | 95.21 ± 8.0 | 72.11 ± 6.42 | 79.03 ± 8.19 | |
| Papain hydrolysates | 90.11 ± 11.34 | 65.32 ± 5.0 | 60.31 ± 6.23 | |

Example 4

The casein-derived hydrolysate digest prepared in example 1 was subjected to Caco-2 mimicking intestinal endothelial cell absorption.

Figure 1:
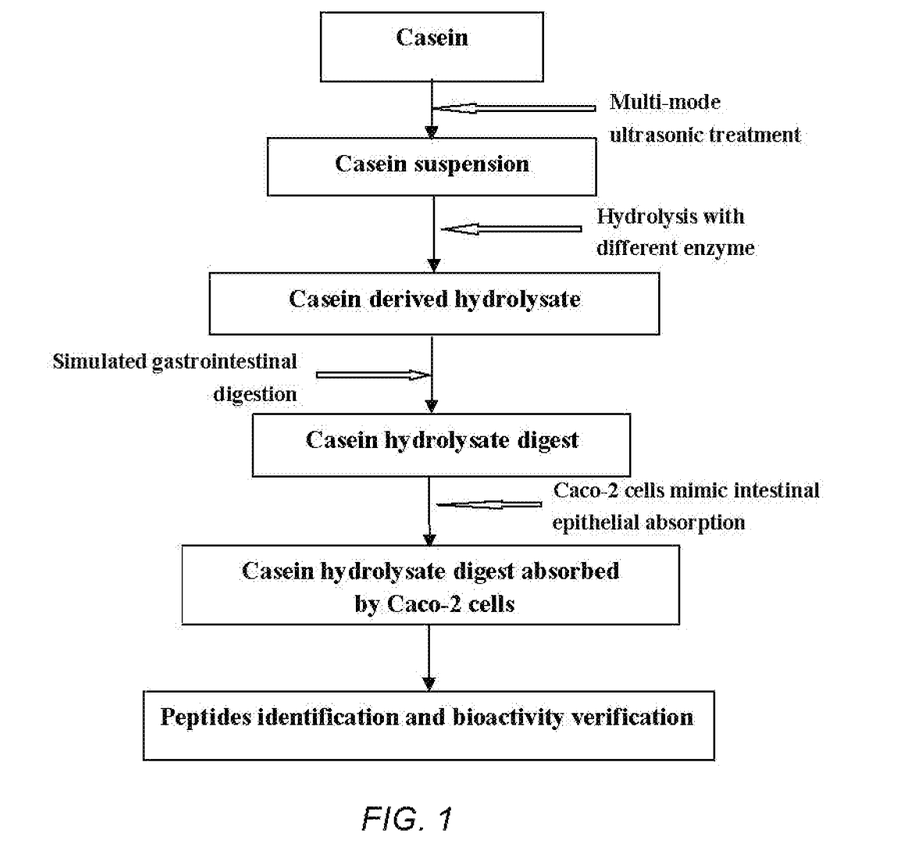
FIG. 1 is a technical route diagram of ultrasound-assisted enzymolysis coupled to simulated gastrointestinal digestion and absorption to prepare casein-derived peptides.
Figure 2:
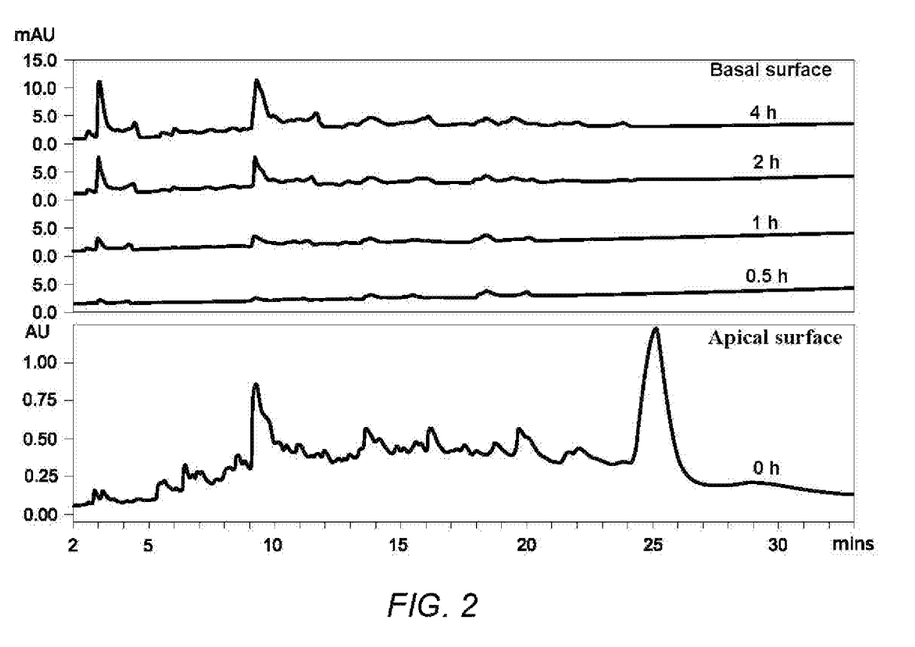
FIG. 2 shows chromatographic profiles of digests derived from casein hydrolysate before and after transcellular transport at 0.5, 1.0, 2.0 and 4.0 h (A).
Figure 3:
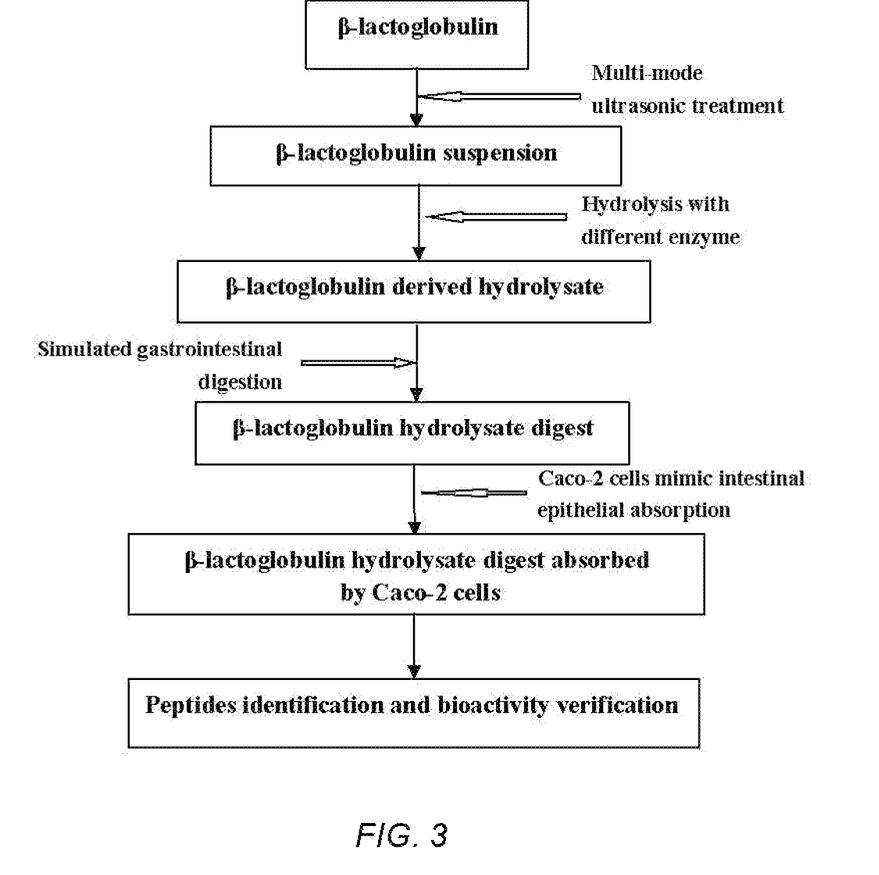
FIG. 3 is a technical route diagram of ultrasound-assisted enzymolysis coupled to simulated gastrointestinal digestion and absorption to prepare β-LG-derived peptides.

The cytotoxicity of the casein-derived hydrolysate digest to Caco-2 cells was first detected. The absorption model of Caco-2 cells mimicking intestinal endothelial cells was built As shown in Table 3, the addition of casein-derived hydrolysate digest increased the viability of Caco-2 cells, indicating that casein-derived hydrolysate digest didn't have any toxicity in Caco-2 cells and helped the growth of Caco-2 cells. As shown in FIG. 1, the absorption of the casein-derived hydrolysate digest from the AP to BL surface increased with time and reached 2.31% at 4 h, indicating selective absorption of peptides in Caco-2 cells. The absorbed digest obtained from the BL surface at the end of 4-hour transport study was tested for its in vitro ACE inhibitory effect and compared to that of the casein hydrolysate digest. After absorption by Caco-2 cells, the $IC_{50}$ value of the ACE inhibitory activity of the casein hydrolysate digest decreased from 55.19 µg/mL to 21.37 µg/mL (Table 2). The above results showed that the ACE inhibitory activity of casein polypeptide was significantly enhanced by Caco-2 cells mimicking intestinal endothelial cells absorption, which indicates that the absorbed polypeptide displayed stronger ACE inhibitory activity than the digest. The absorbed peptides were subjected to LC-ESI-MS/MS analysis. The small peptides with strong ionic strength were chosen out, synthesized and further assayed for their ACE inhibitory activity. Three peptides with high ACE inhibition, Leu-Gln-Pro-Pro (LQPP) (SEQ ID No. 1). Ala-Pro-Tyr (APY) (SEQ ID No. 2), Leu-Ser-Leu-Pro (LSLP) (SEQ ID No. 3) were chosen out; their $IC_{50}$ were 14.21 µM, 19.12 µM, and 21.09 µM, respectively (Table 4).

TABLE 3

Cytotoxicity of casein hydrolysate derived digests at different concentration in Caco-2 cells

| | Concentration of digest (mg/Ml) | Caco-2 viability |
|---|---|---|
| Control | — | 100 |
| Group 1 | 5 | 109.8 ± 5.3 |
| Group 2 | 10 | 119.2 ± 8.5 |
| Group 3 | 20 | 110.2 ± 10.6 |
| Group 4 | 50 | 103.6 ± 9.8 |

TABLE 4

The peptides that are absorbed by Caco-2 cells were sequenced, identified and chemically synthesized to validate the ACE inhibitory activity of the identified peptides.

| Peptide sequence | $IC_{50}$ of ACE inhibitory activity (μg/mL) |
|---|---|
| LQPP | 14.21 |
| APY | 19.12 |
| LSLP | 71.09 |

Experimental method and examples of ultrasound-assisted simulated digestion and absorption method for β-LG derived inflammatory peptide 2. Experimental Method 2.1 Degree of Hydrolysis (DH) and Protein Conversion Rate The DH of β-LG determined using the pH-state method, DH is defined as the percentage of cleaved peptide bonds, which was calculated using the equation below:

$$DH\ (\%) = \frac{V \times N}{\alpha \times M \times h_{tot}} \times 100\%$$

Where, V is the titrant volume of NaOH (mL), N is the concentration of NaOH (mol/L), a is the degree of dissociation of $\alpha$-$NH_2$ (0.99 for β-LG), M is the mass of protein (g), and hr is the number of peptide bonds in the substrate, different proteins had different values of ha, the empirical value of β-LG is $h_{tot}$=7.35 mol/g.

The total nitrogen content of the β-LG and its derived hydrolysate was determined by the Kjeldahl method, and the conversion rate of β-LG was calculated as follows:

Protein conversion rate (%)=hydrolysate nitrogen content/substrate protein nitrogen content*100%

2.2 Cell Culture

The endothelial cell line, EA.hy926 (CRL-2922™), and human colon adenocarcinoma cell line, Caco-2 (HTB-37), were purchased from American-type culture collection (ATCC, Manassas, Va., USA). DMEM supplemented with 10% FBS, 2.5% HEPES, 1% antibiotics, and 1% non-essential amino acids was used as the cell growth medium. The cells were incubated in a humidified atmosphere with 5% $CO_2$ at 37° C. The medium was replaced for three times for every week, and the cells were subcultured using 0.25% trypsin-EDTA treatment.

2.3 Measurement of Cytotoxicity

The cell cytotoxic properties were monitored using an Alamar Blue assay. Caco-2 cells were seeded in 96-well plates at a density of $1\times10^4$ cell/well for 24 h. Then the cells were treated with various concentrations (10-50 mg/mL) of β-LG hydrolysate for another 24 h in a fresh medium. After the 24 h treatment, the media was discarded, and the fresh medium with 10% Alamar Blue reagent was added and incubated for 4 h at 37° C. The fluorescence intensity of the wells was measured at an emission wavelength of 590 nm and an excitation wavelength of 560 nm. The viability of the treated cells was expressed as a percentage as compared to untreated cells.

2.4 Measurement of Anti-Inflammatory Activity

The peptides were subjected to study the anti-inflammatory activity; the levels of intercellular adhesion molecule (ICAM-1) and vascular cell adhesion molecule (VCAM-1) expressed in EA.hy926 cells were detected by Western blot as inflammatory biomarkers. The EA, hy926 cells with passage number <12 were grown in 48-well plates. The cells reaching 80-90% confluence were treated with various concentrations (2.5 mg/mL of hydrolysates and digests, 0.2 mM and 3.0 mM of synthetic peptides) of the samples for 18 h. Then the cells were stimulated with TNF-α at 10 ng/mL and incubated for an additional 6 h in order to induce inflammation.

After the treatment period, the culture medium of the EA. hy926 cells was discarded and a boiling Laemmle buffer containing 0.2% TritonX-100 and 50 μM dithiothreitol was added to lysate the cells. The cell lysates were then run on 9% sodium dodecyl sulfate polyacrylamide gel electrophoresis. The gels were transferred onto nitrocellulose membranes, and immunoblotted with anti-ICAM-1/anti-VCAM-1 antibodies. The concentration of antibody to α-tubulin used was 0.4 μg/mL, while that for all other antibodies was 0.1 μg/mL. The protein bands were scanned using Licor Odyssey BioImager (Licor Biosciences, Lincoln, NB, USA) and quantified by densitometry using Image Studio Lite 5.2. All the data were expressed as the percentage change of the corresponding positive control (cells treated with TNF-α alone).

2.5 Simulated Intestinal Epithelium Absorption Using Caco-2 Cells

The samples collected from the AP and BL surfaces of Caco-2 cells were analyzed on an Acquity Ultra-Performance Liquid Chromatograph (UPLC) system with an Acquity UPLC BEH Cis column (100 mm×2.1 mm i.d., 1.7 μm, Waters, Milford, Mass., USA) using an injection volume of 15 μL. Mobile phases were solvent A (1% TFA in Milli-Q water) and solvent B (1% TFA in acetonitrile). The peptides were eluted with a gradient of solvent A (100-75% in 25 min, 75-50% in 25-35 min) at a flow rate of 0.3 ml/min. The elution was monitored at 220 nm. Absorption was expressed as the percentage of total peak area calculated at different time points (0.5 h, 1 h, 2 h and 4 h) in the BL surface as compared to 0 h in the AP surface.

2.6 Identification of β-Lg-Derived Peptides

The liquid chromatography column used in this study was nanoACQUITY BEH130 $C_{18}$ (75 μm×150 mm, 1.7 μm). The solvent A was acetonitrile (ACN) containing 0.1% formic acid. The peptides were separated using the following gradient: solvent B was water with 0.1% formic acid increasing from 1% to 6% B in 2 min, to 25% B in 23 min, to 45% B in 15 min, to 75% B in 5 min, to 95% B in 5 min, and keeping at 95% B for 5 min. The mass spectrometer was operated in a positive mode with a capillary voltage of 3.5 kV and a source temperature of 100° C. Spectra were recorded over the m/z ranges of 200-1000 in MS mode and in 50-1990 MS/MS mode. The amino acid sequences of peptides were analyzed using Mass Lynx software (Micromass U.K. Ltd.). Peaks Viewer 4.5 (Bioinformatics Solutions Inc., Waterloo, ON, Canada), in combination with manual de novo sequencing was used to process the MS/MS data. Identified peptide sequences were synthesized (>98% purity) by Genscript Corp (Piscataway, N.J.) and used for the bioactivity assays.

The method for extracting β-lactoglobulin with the present invention was as follows: A concentration of 7% (w/v) whey protein solution was prepared by adding whey protein to 7% NaCl water, adjusting the pH to 2 with HCl solution, and centrifuging at 5000 rpm for 20 min to collect the supernatant. Then the supernatant was dialyzed using a dialysis bag with a molecular weight cut off of 14000 Da, and placed in 30 volumes of distilled water for 20 h. Then the retentate in the dialysis bag, i.e. β-LG, was collected.

Example 5

Ultrasound treatment of β-LG. The 200 mL of β-LG with a concentration of 1 g/mL was treated by ultrasound equipment. The ultrasound treatment conditions are as follows: treatment time 30 min; intermittent ratio 10 s/3 s; temperature 30° C. Single frequency ultrasound of 40 kHz was used for the sample treatment.

Enzymolysis of β-LG. After ultrasound treatment, the β-LG suspensions were preheated to 50° C. and adjusted to pH 8.0 with 1.0 M NaOH. Alcalase (the ratio of E'S was 1:20) (w/w) was added to initialize the reaction, and the enzymolysis time was 2 h. The mixture was heated and maintained at 100° C. for 10 min to terminate the reaction. Then the mixture was adjusted to pH 7.0 and centrifuged; the supernatant was collected, desalted, concentrated, and freeze-dried to a powder. The DH and CR of the β-LG, and the anti-inflammatory activity of β-LG-derived hydrolysate, were determined.

Simulated GI digestion. Simulated gastric and intestinal fluids were prepared according to the U.S. Pharmacopeia. Briefly, β-LG-derived hydrolysate was digested with gastric fluid at 1:20 (w/v) for 4 h in a shaking incubator with 120 rpm at 37° C. Then the pH was adjusted to 6.8 and pancreatin was added at 1:100 (w/v) to form the intestinal fluid. The mixture was incubated for a further 6 h to mimic intestinal digestion. The digestion was terminated in boiling water for 10 min. The digest was cooled down and centrifuged at 10.000 g for 10 min to collect the supernatant, which was further centrifuged, desalted, concentrated, and freeze-dried to a powder. The anti-inflammatory activity of the 4 h's and 10 h's β-LG hydrolysate digest was measured.

As shown in Table 5, after single frequency ultrasound pretreatment, the DH of β-LG increased from 10.32% to 13.70%, the protein conversion rate increased from 30.27% to 35.17%. Alcalase hydrolysate showed good anti-inflammatory activity, the expression of the VCAM-1 and ICAM-1 were 42.3% and 62.7%, respectively (Table 6). After simulated gastric digestion, the β-LG hydrolysate digest showed good anti-inflammatory activity, and the expression of the VCAM-1 and ICAM-1 was 48.2% and 55.3%, respectively. After simulated intestinal digestion, the β-LG hydrolysate digest still showed good anti-inflammatory activity, and the expression of the VCAM-1 and ICAM-1 was 50.7% and 63.2%, respectively. Simulated gastrointestinal digestion appeared to have minimal effect on the anti-inflammatory activity of β-LG hydrolysates.

Example 6

Ultrasound treatment of β-LG. The 200 mL of β-LG with a concentration of 4 g/mL was treated by ultrasound equipment. The ultrasound treatment conditions are as follows: treatment time 20 min; intermittent ratio 10 s/3 s; temperature 25° C. Dual-frequency simultaneous ultrasound with 20/28 kHz was used for the sample treatment.

Enzymolysis of β-LG. After ultrasound treatment, the β-LG suspensions were preheated to 55° C. and adjusted to pH 7.5 with 1.0 M NaOH. Neutral protease (the ratio of E/S was 1:30) (w/w) was added to initial the reaction and the enzymolysis time was 4 h. The mixture was heated and maintained at 100° C. for 10 min to terminate the reaction. Then the mixture was adjusted to pH 7.0 and centrifuged; the supernatant was collected, desalted, concentrated, and freeze-dried to a powder. The DH and CR of the β-LG, and the anti-inflammatory activity of β-LG-derived hydrolysate, were determined.

Simulated GI digestion. β-LG-derived hydrolysate was subjected to simulated gastric and intestinal digestion. Simulated gastric and intestinal fluids were prepared according to the U.S. Pharmacopeia. Briefly, β-LG-derived hydrolysate was digested with gastric fluid at 1:30 (w/v) for 3 h in a shaking incubator with 150 rpm at 37° C. Then the pH was adjusted to 6.8 and pancreatin was added at 1:100 (w/v) to form the intestinal fluid. The mixture was incubated for a further 4 h to mimic intestinal digestion. The digestion was terminated in boiling water for 10 min. The digest was cooled down and centrifuged at 10,000 g for 10 min to collect the supernatant, which was further centrifuged, desalted, concentrated, and freeze-dried to a powder. The anti-inflammatory activity of the 4 h's and 10 h's β-LG hydrolysate digest was measured.

As shown in Table 5, after dual-frequency simultaneous ultrasound pretreatment, the DH of β-LG increased from 6.19% to 9.53%, the protein conversion rate increased from 15.11% to 22.34%. Neutral protease hydrolysate showed good anti-inflammatory activity, and the expression of the VCAM-1 and ICAM-1 was 63.2% and 52.3%, respectively. The simulated gastric digestion of the β-LG hydrolysate digest resulted in good anti-inflammatory activity, and the expression of the VCAM-1 and ICAM-1 was 50.3% and 47.3%, respectively. Also, the simulated intestinal digestion of the β-LG hydrolysate digest showed good anti-inflammatory activity, and the expression of the VCAM-1 and ICAM-1 was 53.4% and 53.8%, respectively. Simulated gastrointestinal digestion appeared to have minimal effect on the anti-inflammatory activity of β-LG hydrolysates.

Example 7

Ultrasound treatment of β-LG. The 200 mL of β-LG with a concentration of 4 g/mL was treated by ultrasound equipment. The ultrasound treatment conditions are as follows: treatment time 10 min; intermittent ratio 10 s/3 s; temperature 25° C. Triple-frequency simultaneous ultrasound with 20/28/40 kHz was used for the sample treatment.

Enzymolysis of β-LG. After ultrasound treatment, the β-LG suspensions were preheated to 70° C. and adjusted to pH 8 with 1.0 M NaOH. Thermolysin (the ratio of E/S was 1:50) (w/v) was added to initial the reaction and the enzymolysis time was 2 h. The mixture was heated and maintained at 100° C. for 10 min to terminate the reaction. Then the mixture was adjusted to pH 7.0 and centrifuged, the supernatant was collected, desalted, concentrated, and freeze-dried to a powder. The DH and CR of the β-LG, and the anti-inflammatory activity of β-LG-derived hydrolysate, were determined.

Simulated GI digestion. β-LG-derived hydrolysate was subjected to simulated gastric and intestinal digestion. Simulated gastric and intestinal fluids were prepared according to the U.S. Pharmacopeia. Briefly, β-LG-derived hydrolysate was digested with gastric fluid at 1:50 (w/v) for 2 h in a shaking incubator with 180 rpm at 37° C. Then the pH was adjusted to 6.8 and pancreatin was added at 1:100 (w/v) to form the intestinal fluid. The mixture was incubated for a further 4 h to mimic intestinal digestion. The digestion was terminated in boiling water for 10 min. The digest was cooled down and centrifuged at 10,000 g for 10 min to collect the supernatant, which was further centrifuged, desalted, concentrated, and freeze-dried to a powder. The anti-inflammatory activity of the 4 h's and 10 h's β-LG hydrolysate digest was measured.

As shown in Table 5, after triple-frequency simultaneous ultrasound pretreatment, the DH of β-LG increased from 13.20% to 21.41%, the protein conversion rate increased from 36.90% to 41.02%.

Example 8

The β-LG-derived hydrolysate digest prepared in example 7 was subjected to Caco-2 mimicking intestinal endothelial cell absorption.

The cytotoxicity of the β-LG-derived hydrolysate digest to Caco-2 cells was first detected. The absorption model of Caco-2 cells mimicking intestinal endothelial cells was built as follows: Caco-2 cells were grown in 12-well Transwell® plates at a concentration of $2\times10^5$ cells/mL. The medium of the cell was replaced every other day. After 21 days of cell culture, some evaluation indicators of the Caco-2 cells were measured, including epithelial cell resistance, alkaline phosphatase activity and sodium fluorescein leakage test. Before initiation of the transport experiments, the Caco-2 cells was washed by an HBSS buffer; and 0.5 mL of the β-LG hydrolysate digest (20 mg/mL, dissolved in an HBSS buffer)

TABLE 5

Effects of ultrasound pretreatment on the DH, CR of β-LG hydrolysates by different enzymatic hydrolysis

| | Traditional hydrolysis | | Ultrasound assisted hydrolysis | | |
|---|---|---|---|---|---|
| Enzyme | DH (%) | CR (%) | Ultrasound mode | DH (%) | CR (%) |
| Akalase | 10.32 ± 1.73 | 30.27 ± 0.91 | 40 kHz | 13.70 ± 1.09 | 35.17 ± 1.77 |
| Neutral protease | 6.19 ± 0.42 | 15.11 ± 0.37 | 20/28 kHz | 9.53 ± 0.97 | 22.34 ± 1.45 |
| Thermolysin | 13.20 ± 0.54 | 36.90 ± 0.64 | 20/28140 kHz | 21.41 ± 2.31 | 41.02 ± 2.00 |

Thermolysin hydrolysate showed good anti-inflammatory activity, and the expression of the VCAM-1 and ICAM-1 was 48.9% and 36.5%, respectively. After simulated gastric digestion, the β-LG hydrolysate digest showed good anti-inflammatory activity, and the expression of the VCAM-1 and ICAM-1 was 43.3% and 30.1%, respectively. After simulated intestinal digestion, the β-LG hydrolysate digest still showed good anti-inflammatory activity, and the expression of the VCAM-1 and ICAM-1 was 49.1% and 36.2%, respectively (Table 6). Simulated gastrointestinal digestion appeared to have minimal effect on the anti-inflammatory activity of β-LG hydrolysates.

was adding to the AP surface; 1.5 mL of HBSS buffer was added to the BL surface; then the Caco-2 cells were incubated for 4 h at 37° C. 0.2 mL of AP surface samples at 0 h, and BL surface samples at 0.5, 1, 2, and 4 h were collected for the absorption detection. The AP (apical) surface samples and BL (basolateral) surface samples at 4 h were collected for the anti-inflammatory activity detection, respectively. The β-LG hydrolysates digests and its absorbed digests subjected to the amino acid sequences analysis by UPLC-MC. Some small peptides with strong ionic strength were screened out, synthesized, and detected for anti-inflammatory activity.

TABLE 6

Effects of different β-LG hydrolysates before gastric digestion, after gastric digestion, intestinal digestion and Caco-2 cells absorption on TNF-α-induced VCAM-1 and ICAM-1 protein expression in EA.hy926 cells

| β-LG-derived hydrolysates | TNF-α (6h) | Before gastric digestion | | After gastric digestion | | After intestinal digestion | | After Caco-2 cells absorption | |
|---|---|---|---|---|---|---|---|---|---|
| | | VCAM-1 (% TNF-α alone) | ICAM-1 (% TNF-α alone) | VCAM-1 (% TNF-α alone) | ICAM-1 (% TNF-α alone) | VCAM-1 (% TNF-α alone) | ICAM-1 (% TNF-α alone) | VCAM-1 (% TNF-α alone) | ICAM-1 (% TNF-α alone) |
| — | − | 12.1 ± 1.1 | 13.3 ± 2.8 | 14.5 ± 0.9 | 16.2 ± 2.0 | 11.9 ± 1.2 | 12.3 ± 0.79 | | |
| — | + | 100 | 100 | 100 | 100 | 100 | 100 | | |
| Alcalase hydrolysate | + | 42.3 ± 7.1 | 62.7 ± 10.5 | 48.2 ± 8.6 | 55.3 ± 6.2 | 50.7 ± 7.0 | 63.2 ± 7.8 | | |
| Neutral protease hydrolysate | + | 63.2 ± 7.5 | 52.3 ± 7.3 | 50.3 ± 7.0 | 47.3 ± 7.1 | 53.4 ± 6.5 | 53.8 ± 8.4 | | |
| Thermolysin hydrolysate | + | 48.9 ± 8.8 | 36.5 ± 4.9 | 43.3 ± 6.3 | 30.1 ± 3.3 | 49.1 ± 13.2 | 36.2 ± 5.5 | 22.1 ± 1.7 | 16.9 ± 2.4 |

TABLE 7

Cytotoxicity of β-LG hydrolysate derived digests at different concentration in Caco-2 cells

| | Concentration of digest (mg/Ml) | Caco-2 viability |
|---|---|---|
| Control | — | 100 |
| Group 1 | 5 | 125.8 ± 4.7 |
| Group 2 | 10 | 124.3 ± 9.0 |
| Group 3 | 20 | 110.2 ± 10.8 |
| Group 4 | 50 | 106.5 ± 8.0 |

As shown in Table 7, the addition of β-LG-derived hydrolysate digest increased the viability of Caco-2 cells, indicating that β-LG-derived hydrolysate digest didn't have any toxicity in Caco-2 cells. As shown in Table 8, the absorption of the β-LG-derived hydrolysate digest from the AP to BL surface increased with time and reached 2.67% at 4 h, indicating selective absorption of peptides in Caco-2 cells. After absorption by Caco-2 cells, the anti-inflammatory activity of the β-LG hydrolysate digest largely increased. The expression of the VCAM-1 and ICAM-1 of the absorption digest was 22.1% and 16.9%. Compared to the thermolysin hydrolysate digest, the expression of VCAM-1 and ICAM-1 of the absorption digest decreased by 17.0% and 19.3% (Table 6).

TABLE 8

Transcellular absorption of digests derived from β-LG hydrolysates was monitored in Caco-2 cell monolayers at 0.5, 1.0, 2.0 and 4.0 h

| Absorption time (h) | Absorption percentage (%) |
|---|---|
| 0.5 | 0.22 ± 0.01 |
| 1 | 0.71 ± 0.02 |
| 2 | 1.35 ± 0.01 |
| 4 | 2.67 ± 0.03 |

The above results showed that the anti-inflammatory activity of β-LG polypeptide was significantly enhanced by Caco-2 cells mimicking intestinal endothelial cells absorption, which indicated that the absorbed polypeptide displayed stronger anti-inflammatory activity than the digest. The β-LG hydrolysate digests and their absorbed digests were subjected to identification and analysis. Some small peptides with strong ionic strength were chosen out, synthesized and further assayed for their anti-inflammatory activity. Two peptides with high anti-inflammatory activity, Phe-Tyr-Gln-Ala (FYQA) (SEQ ID No. 4). Leu-Gln-Tyr (LQY) (SEQ ID No. 5) were chosen out. These two peptides strongly inhibited the expression of VCAM-1 and ICAM-1 of these two peptides, which was 41.3% and 56.6%, 33.7% and 48.2%, respectively (Table 9).

TABLE 9

The β-LG derived peptides that are absorbed by Caco-2 cells were sequenced, identified and chemically synthesized to validate the anti-inflammatory activity of the identified peptides.

| Peptide sequence | Concentration (µM) | TNF-α | VCAM-1 (TNF-α) | ICAM-1 (%TNF-α) |
|---|---|---|---|---|
| | | − | 16.2 ± 7.2 | 12.6 ± 13.3 |
| | | + | 100 | 100 |
| FYQA | 100 | + | 41.3 ± 10.6 | 56.6 ± 9.0 |
| LQY | 100 | + | 33.7 ± 6.9 | 48.2 ± 6.3 |

The invention claimed is:

1. A method for preparing a β-lactoglobulin (β-LG)-derived anti-inflammatory peptides, which is characterized by the following steps:
   (1) extraction of β-LG: a concentration of 7% (w/v) whey protein solution is prepared by adding whey protein to 7% NaCl water, adjusting the pH to 2 with HCl, and centrifuging at 5000 rpm for 20 minutes to collect supernatant, then the supernatant is dialyzed using a dialysis bag with a molecular weight cut off of 14,000 Da, placed in 30 volumes of distilled water for 20 hours and retentate in the dialysis bag, β-LG, is collected;
   (2) ultrasound treatment of β-LG: the β-LG with a concentration of 1 g/mL-4 g/mL is treated by an ultrasound equipment;
   (3) enzymolysis of β-LG: after ultrasound treatment, the β-LG suspensions are preheated to 50° C.-70° C. and adjusted to pH 7.5-8.0 with 1.0 M NaOH, a protease (the ratio of protease to β-LG is 1:20-1:50) (w/w) is added to initiate the reaction and the enzymolysis time is 2-4 hours, the mixture is heated and maintained at 100° C. for 10 minutes to terminate the reaction, then the mixture is adjusted to pH 7.0 and centrifuged; the supernatant is collected, desalted, concentrated, and freeze-dried to a powder; wherein said protease is selected from the group consisting of alcalase, neutral protease and thermolysin,
   (4) simulated GI digestion: β-LG-derived hydrolysate is subjected to simulated gastric and intestinal digestion, β-LG-derived hydrolysate is digested with gastric fluid at 1:20-1:50 (w/v) for 2-4 hours in a shaking incubator with 120-180 rpm at 37-° C. then the pH is adjusted to 6.8 and pancreatin is added at 1:100 (w/v) to form an intestinal fluid, the mixture is incubated for 4-6 h to mimic intestinal digestion, the digestion is terminated in boiling water for 10 minutes, the digest is cooled down and centrifuged at 10,000 g for 10 minutes to collect the supernatant, which is further centrifuged, desalted, concentrated, and freeze-dried to a powder;
   (5) simulated intestinal epithelium absorption: a Caco-2 cells transport model is constructed, a concentration of 20 mg/mL β-LG hydrolysate digest is prepared by dissolving in an HBSS buffer, absorption of the casein hydrolysate digests is evaluated by adding the digests to an apical (AP) surface, basal (BL) surface samples at 0.5-4 hours are collected, desalted, concentrated, and freeze-dried;
   (6) characterization of the β-LG derived peptides: the β-LG derived peptides absorbed by the Caco-2 cells transport model in step (5) are subjected to liquid chromatography-electrospray ionization tandem mass spectrometry (LC-ESI-MS/MS) analysis, the peptides with less than 500 Da are selected;
   (7) the selected peptides in step (6) are synthesized and assayed for their anti-inflammatory activity, and the β-LG-derived peptide showing anti-inflammatory activity is:
   Phe-Tyr-Gln-Ala (SU ID NO:4).

2. The method for preparing the β-lactoglobulin-derived anti-inflammatory peptide according to claim 1, wherein the ultrasound treatment conditions in the step (2) are as follows: treatment time of 10 minutes-30 minutes; intermittent ratio of 10 seconds on/3 seconds off; temperature 25° C., wherein the ultrasound frequency used is selected from a single-frequency ultrasound of 20, 28 or 40 kHz, a dual-frequency simultaneous ultrasound of 20/40, 20/28 or 28/40 kHz and a triple-frequency simultaneous ultrasound of 20/28/40 kHz wherein the protease of step (3) is neutral protease, or thermolysin.

3. The method for preparing the β-lactoglobulin-derived anti-inflammatory peptide according to claim 1, wherein the protease of the step (3) is thermolysin; and the ultrasound is triple-frequency simultaneous ultrasound of 20/28/40 kHz.

4. The method for preparing the β-lactoglobulin-derived anti-inflammatory peptide according to claim 1, wherein the protease of the step (3) is alcalase.

5. An anti-inflammatory peptide consisting of the amino acid sequence Phe-Tyr-Gln-Ala (SEQ ID NO:4).

* * * * *